US00PP23122P2

(12) United States Plant Patent
Kordes

(10) Patent No.: US PP23,122 P2
(45) Date of Patent: Oct. 23, 2012

(54) FLORIBUNDA ROSE PLANT NAMED 'KORSCHWILL'

(50) Latin Name: *Rosa hybrida*
Varietal Denomination: KORschwill

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,871

(22) Filed: Jul. 14, 2011

(51) Int. Cl.
*A01H 5/00* (2006.01)

(52) U.S. Cl. ..... Plt./150

(58) Field of Classification Search ..... Plt./150
See application file for complete search history.

*Primary Examiner* — Annette Para

(57) ABSTRACT

A new and distinct variety of rose with long lasting, novel red flowers, and attractive foliage with good disease resistance. It exhibits uniform, upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORschwill'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2000. The crossing was between an 'un-named seedling', and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORschwill'.

SUMMARY OF THE INVENTION

The new rose plant may be distinguished from its seed parent, an 'un-named seedling', by the following combination of characteristics:

1. The flower color of 'KORschwill' is velvet red while the flower color of the seed parent is dark red.
2. The disease resistance of 'KORschwill' is excellent while the disease resistance of the seed parent is only good.

The new rose plant may be distinguished from its pollen parent, an 'un-named seedling' by the following combination of characteristics:

1. The flower color of 'KORschwill' is velvet red while the flower color of the pollen parent is pink.
2. The growth habit of 'KORschwill' is moderately upright to bushy while the growth habit of the pollen parent is upright.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORschwill' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORschwill' was selected in 2001 from the seedling beds to be asexually propagated for further evaluation. The first asexual propagation of 'KORschwill' was done by budding to seedling understocks in July, 2001 at the inventor's nursery in Offenseth-Sparrieshoop, Germany.

This initial and other subsequent propagations conducted in controlled environments demonstrate that 'KORschwill' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORschwill'.

DETAILED BOTANICAL DESCRIPTION

The following is a description of 'KORschwill', as observed growing in June, 2011 in a nursery in Jackson County, Oreg., on plants of 3 years of age. Color references are made using The Royal Horticultural Society (London, England) Colour Chart, 2001 except where common terms of color are used.

For a comparison, several physical characteristics of the rose variety 'KORtemma', a rose variety from the same inventor described and illustrated in U.S. Plant Pat. No. 9,115 and issued on Apr. 25, 1995 are compared to 'KORschwill' in Chart 1.

CHART 1

| Characteristic | 'KORschwill' | 'KORtemma' |
|---|---|---|
| Flower bud size; upon opening: | 25 mm (l). | 19 mm (l). |
| Plant vigor: | Moderately vigorous. | Vigorous. |
| Prickle shape: | Concave. | Hooked downward. |

Parents:

*Seed parent.*—an 'un-named seedling'.

*Pollen parent.*—an 'un-named seedling'.

Classification:

*Botanical classification.*—*Rosa hybrida* 'KORschwill'.

*Commercial classification.*—Floribunda rose.

FLOWER AND FLOWER BUD

Blooming habit: Recurrent.

Flower bud:

*Size.*—Upon opening, 25 mm in length from base of receptacle to end of bud and 20 mm diameter at its widest point.

*Bud form.*—Short. Globular.

*Bud color.*—As sepals first unfold, bud color is Red Group 46A. When ¼ open, the upper surface of petals is Red Group 45B, and the lower surface is Red Group 46A. The guard petals are Greyed-Green 198B in upper and mid petal areas and Yellow-Green Group 145C in lower petal area.

*Sepals.*—Color: Upper surface Yellow-Green Group 146D. Lower surface Yellow-Green Group 144B with intonations of Greyed-Purple Group 185C. Size: Average 25 mm (l)×8 mm (w). Shape: Weak foliaceous appendages on two of the five sepals. Apex: Apiculate. Base: Flat at union with receptacle. Quantity: Five. Surface texture: Upper side: Dense pubescence. Lower surface: Slight pubescence. Margins: Mostly smooth, except that here are limited numbers of stipitate glands along the basal zone.

Receptacle:

*Surface.*—Smooth, shiny.

*Color.*—Between Yellow-Green Group 144A and 144B.

*Shape.*—Pear shaped.

*Size.*—12 mm (h)×8 mm (w).

*Anthocyanin.*—Greyed-Purple Group 187D below sepals.

Peduncle:

*Surface.*—Smooth. With limited number of stipitate glands.

*Length.*—30 to 40 mm average length.

*Diameter.*—2 to 3 mm average diameter.

*Color.*—Yellow-Green Group 146D.

*Strength.*—Strong.

*Borne.*—Multiple flower buds per stem, generally 2 to 4.

*Anthocyanin.*—Greyed-Red Group 182B.

Flower bloom:

*Fragrance.*—None.

*Duration.*—On the plant 4-6 days. Senesced petals drop away cleanly. As a cut flower, 3 to 5 days.

*Size.*—When open, the average flower diameter is 60-70 mm when open. Average flower depth is 35 mm (from top of bloom to base of receptacle).

*Form.*—Shape of flower when viewed from the side: Upon opening, upper part: Flat. Upon opening, lower part: Flattened convex. Open flower, upper part: Flattened convex. Open flower, lower part: Concave.

Color:

*Upon opening, petals.*—Outermost petals: Outer Side: Red Group 53B. Inner Side: Red Group 45A.

*Innermost petals.*—Outer Side: Red Group 53B. Inner Side: Red Group 45B.

*Upon opening, basal petal spots.*—Basal petal spot, outermost petals: Outer Side: White Group 155A. Inner Side: Green-White Group 157D. Basal petal spot, innermost petals: Outer Side: White Group 155D. Inner Side: White Group 155B.

*After opening, petals.*—Outermost petals: Outer Side: Red Group 53C. Inner Side: Red Group 53C. Innermost petals: Outer Side: Red Group 53C. Inner Side: Red Group 45B.

*After opening, basal petal spots.*—Basal petal spot, outermost petals: Outer Side: White Group 155B. Inner Side: Green-White Group 157D. Basal petal spot, innermost petals: Outer Side: White Group 155B. Inner Side: White Group 155B.

General tonality: On open flower Red Group 46B. No change in the general tonality at the end of the 4th day. Afterwards, general tonality is Red Group 53B.

Petals:

*Petal count.*—Semi double. Average Range: Approximately 16-18 petals under normal conditions.

*Petal reflex.*—Petals reflex somewhat.

*Petal edge.*—Slightly ruffled.

*Petal shape.*—Ovate. Apex shape is round. Shape of base is obtuse.

*Petal size.*—30 mm (l)×40 mm (w).

*Thickness.*—Average.

*Petal arrangement.*—Not formal.

Petaloids: Usually a few present.

*Petaloid count.*—Average of 0-3 per flower.

*Petaloid size.*—Petaloids are 2-4 mm long and 1 mm wide.

*Petaloid shape.*—Irregular.

*Petaloid color.*—Edge of the petaloid from basal zone to middle zone is White Group 155D, Red Group 46C on inner and outer sides.

*Petaloid texture.*—Thick.

*Margins.*—Undulated.

*Petaloid shape.*—Apex: Generally pointed. Base: Deltoid.

Reproductive organs:

*Pistils.*—Approximately 12 present. Stigmas: Location: Slightly inferior in position to anthers. Color: Yellow-Green Group 154D. Styles: Length: 5 mm long on average. Color: Yellow-Green Group 1D.

*Stamens.*—Approximately 120 on average and regularly arranged. Anthers: Size: About 1.5 mm long. Pollen: Generally present. Color: Between Greyed-Orange Group 164C and Greyed-Orange Group 165D. Filaments: Color: Yellow-Green Group 144D at base changing to Green-White Group 157A at point of attachment to anther. With intonations of Red Group 48C. Length: About 7 mm.

THE PLANT

Plant growth: Moderately upright to bushy habit. When grown as a field grown plant, the average plant height is 70 cm and the average plant width is 50 cm.

Stems:

*Stem color*.—Young wood: Yellow-Green Group 144A. Older wood: Yellow-Green Group 146D.

*Stem surface*.—Young wood: Smooth. Older wood: Smooth.

Prickles: Present.

*Incidence*.—6-8 per 10 cm of stem.

*Size*.—Average length: 5 mm.

*Color*.—Immature prickles: Greyed-Purple Group 182C. Mature prickles: Greyed-Red Group 183D.

*Shape*.—Concave.

*Anthocyanin*.—None observed.

Leaves and leaflets: Normally 5 leaflets on normal leaves in middle of the stem.

*Venation pattern*.—Pyramidal net pattern.

*Leaf size*.—70 mm (l)×45 mm (w).

*Abundance*.—Average.

*Texture*.—Thick. Upper side of leaflet: Glossy, smooth. Under side of leaflet: Semi-glossy, smooth.

*Color, mature foliage*.—Upper Leaf Surface: Yellow-Green Group 137A. Lower Leaf Surface: Yellow-Green Group 137C.

*Color, juvenile foliage*.—Upper Leaf Surface: Yellow-Green Group 137A. Lower Leaf Surface: Yellow-Green Group 137B. Anthocyanin intonation: Present. Intonations present on juvenile leaflets of Greyed-Purple Group 183C.

Stipules:

*Size*.—About 12 mm long. 1 stipule per compound leaf.

*Stipule color*.—Yellow-Green Group 146B.

*Anthocyanin*.—Greyed-Red Group 187B.

*Stipitate glands*.—Present on margins.

*Shape*.—Apex: Apiculate. Base: Flat.

Petiole:

*Length*.—Average length: 10 mm.

*Diameter*.—Average diameter: 2 mm.

*Petiole color*.—Yellow-Green Group 146C.

*Underneath*.—Fine prickles at point of leaf attachment. Generally smooth, With limited numbers of fine stipitate glands and pubescence.

*Anthocyanin*.—None on mature foliage.

Petiole rachis:

*Length*.—About 15 mm.

*Diameter*.—About 1-2 mm.

*Color*.—Yellow-Green Group 146B.

*Underneath*.—Fine prickles.

*Margins*.—Limited numbers of stipitate glands.

Leaflets:

*Size*.—Average size of the terminal leaflet is 35-45 mm (l)×40 mm (w).

*Shape*.—Base: Obtuse. Apex: Ovate.

*Margins*.—Finely serrated.

*Surface*.—Upper: Glossy. Lower: Matte.

*Texture*.—Thick.

Hips/seed formation: None observed.

Winter hardiness: To date, the variety has been grown successfully in Zones 5-9.

Disease resistance: Very good resistance to Powdery mildew (*Sphaerotheca pannosa*), blackspot (*Diplocarpon rosae*), and rust (*Phragmidium disciflorum*) diseases under normal growing conditions.

I claim:

1. A new and distinct variety of rose plant, as described and illustrated herein.

* * * * *

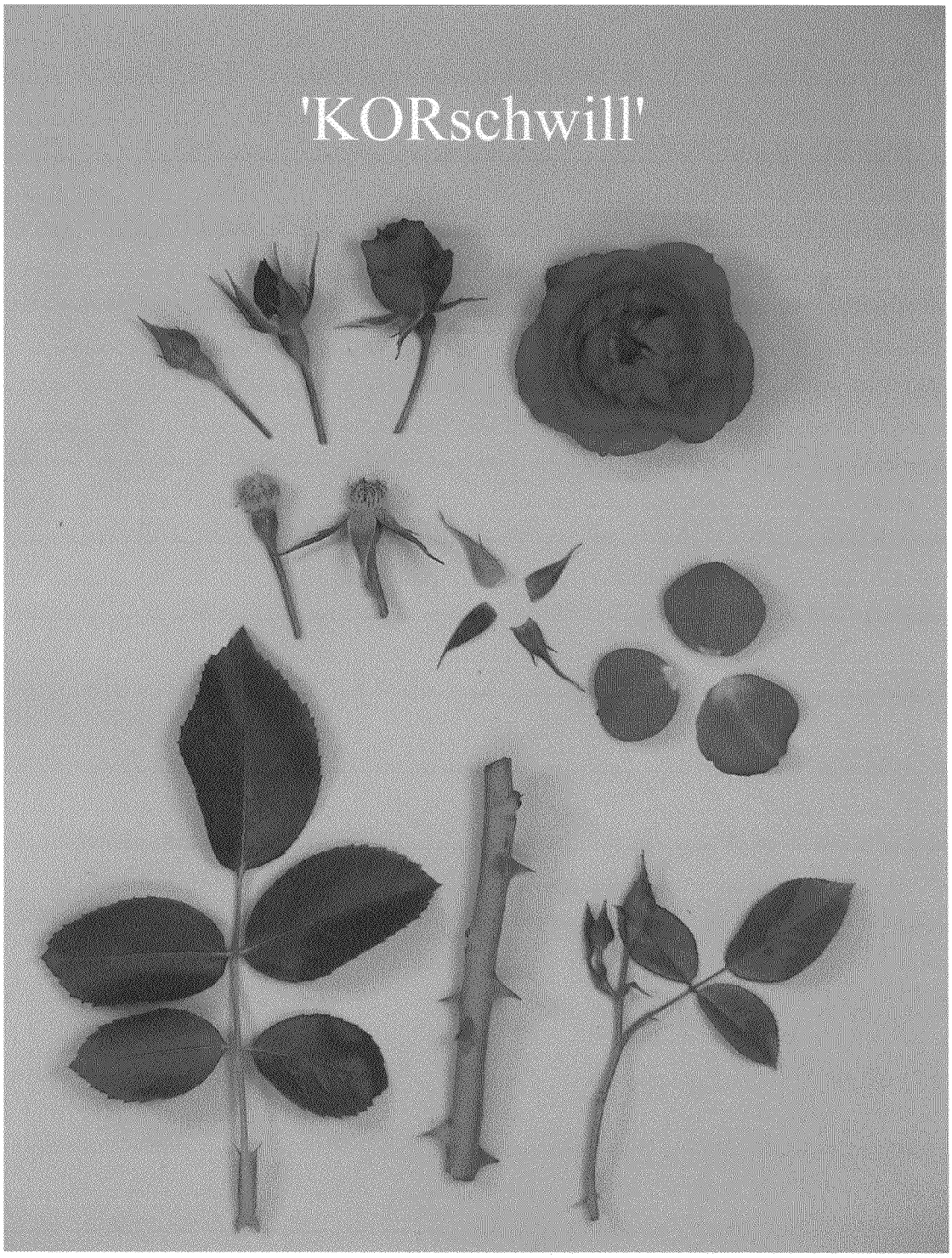
'KORschwill'